United States Patent [19]
Mallasch

[11] Patent Number: 5,417,721
[45] Date of Patent: May 23, 1995

[54] PROSTATE GLAND ENLARGEMENT REDUCING DEVICE

[76] Inventor: Luther F. Mallasch, P.O. Box 2226, Hemet, Calif. 92546

[21] Appl. No.: 177,647

[22] Filed: Dec. 28, 1993

Related U.S. Application Data

[63] Continuation of Ser. No. 897,937, Jun. 15, 1992, abandoned.

[51] Int. Cl.$^6$ ............................................. A61F 7/10
[52] U.S. Cl. .................................. 607/108; 602/2; 220/914
[58] Field of Search ............... 128/401; 602/2; 604/285; 606/20–21, 25; 220/914, DIG. 13; 607/108, 114

[56] References Cited

U.S. PATENT DOCUMENTS

| | | | |
|---|---|---|---|
| 677,489 | 7/1901 | Woods | 220/DIG. 13 |
| 734,213 | 7/1903 | Barnes | 128/401 X |
| 1,744,423 | 1/1930 | Toadvine | 607/114 X |
| 4,240,436 | 12/1980 | Singleton | 607/108 |
| 4,286,596 | 9/1981 | Rubinstein | 604/285 X |
| 4,841,970 | 6/1989 | Rand | 128/401 |
| 4,844,073 | 7/1989 | Pohler | 128/401 |
| 4,938,221 | 7/1990 | Tuffel | 128/401 |
| 5,165,402 | 11/1992 | McCoy | 602/2 X |

FOREIGN PATENT DOCUMENTS

| | | | |
|---|---|---|---|
| 0292913 | 12/1918 | Germany | 607/114 |
| 3906539 | 10/1989 | Germany | 128/401 |
| 1344335 | 10/1987 | U.S.S.R. | 606/21 |
| 8403434 | 9/1984 | WIPO | 604/285 |

*Primary Examiner*—David H. Willse
*Attorney, Agent, or Firm*—Peter Paul Mitrano

[57] ABSTRACT

A device for treating an enlarged prostate which comprises inserting snugly between the legs beneath the outside area of the prostate of a subject afflicted therewith a specially pre-shaped device previously frozen which thereby temporarily relieves the pressure of the prostate gland on the urethra (the tube that passes through the prostate from the bladder to the penis) thereby allowing a man with an enlarged prostate to urinate more freely.

3 Claims, 1 Drawing Sheet

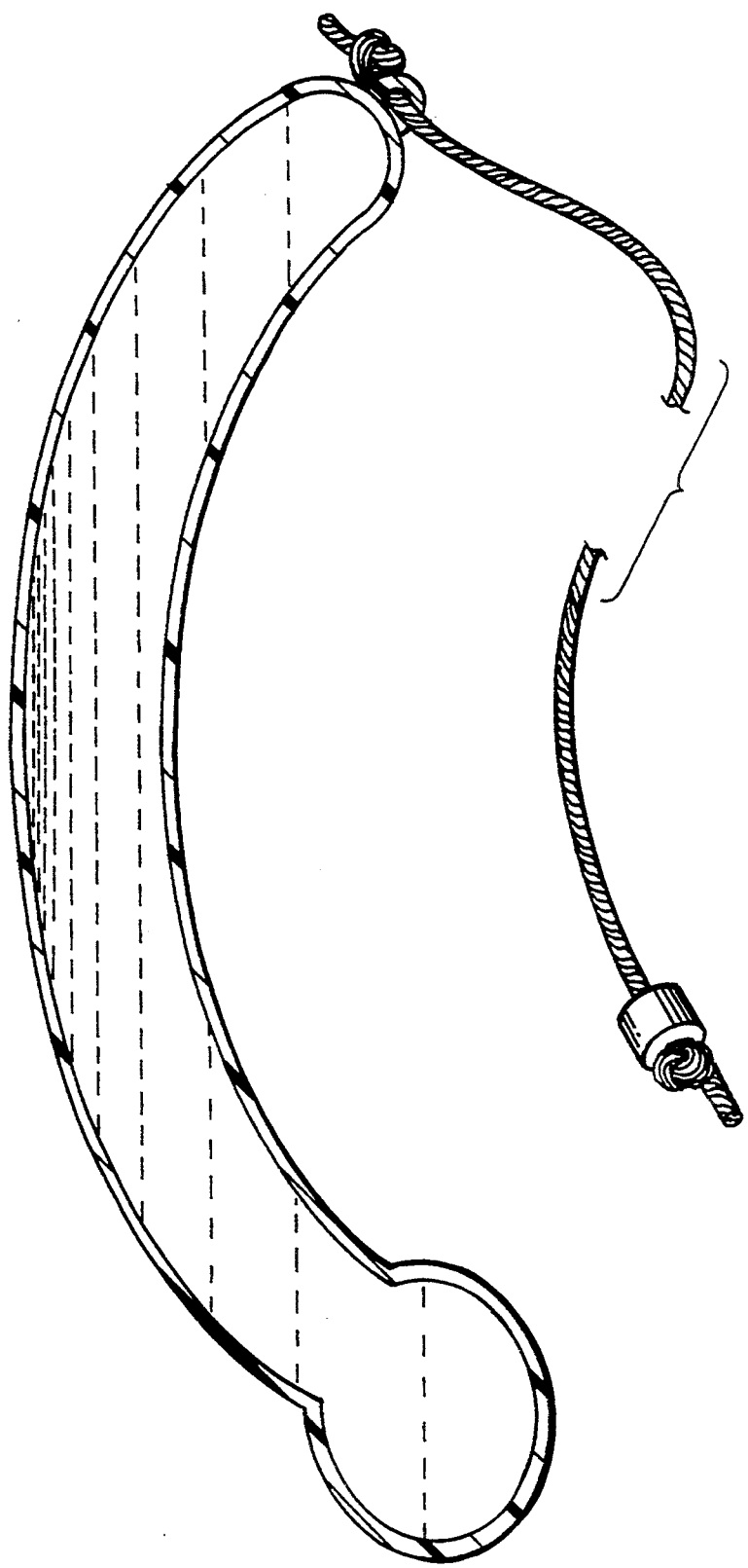

PROSTATE GLAND ENLARGEMENT REDUCING DEVICE

This application is a continuation of U.S. application Ser. No. 07/897,937, filed on Jun. 15, 1992, now abandoned.

The title of the invention is "PROST-COOL". The applicant's name is Luther Ferdinand Mallasch. The applicant is a citizen of the United States of America. The applicant is a resident of the State of California.

BACKGROUND OF INVENTION

The prostate is a gland composed of an outer muscular shell surrounding tissue. The prostate starts out being the size of a pea at the birth of a male. At puberty, there is substantial growth in the prostate. The prostate is fully grown and is the size of a walnut by the time a man reaches the age of thirty. Sometime between the time a man reaches forty or fifty years of age, the prostate can start to enlarge in size.

The prostate grows larger in response to the male hormone testosterone. The tissue of the prostate can enlarge until said tissue constricts the urethra, the tube through which urine empties from the bladder. This can lead to weak flow, infections, incomplete emptying of the bladder and to kidney and bladder damage.

The prostate gland is located below a man's urinary bladder. The prostate gland is connected by the urethra, which is a tube that starts at the urinary bladder and goes through the middle of the prostate gland and carries urine out through the penis. As some men grow older, the prostate tissue surrounding the urethra grows in size and constricts the flow of urine from the urinary bladder to the penis. This can cause a man extreme pain and discomfort.

Surgery is one method of attempting to correct the problem. Surgery involves the removal of some of the enlarged tissue from the prostate. Many men prefer to forego surgery and thus elect to endure the pain. There have been some recent claims that experimental drugs appear to be an effective alternative to surgery; many men are reluctant to experiment with said drugs.

This invention relates to an improved device where the shape provides the means of temporarily reducing the size of the prostate gland. The effectiveness and efficiency of the treatment of the prostate gland is thereby improved. The device is also capable of being reused.

Stoy in U.S. Pat. No. 4,563,182 and Rand in U.S. Pat. No. 4,841,970 suggest rectal inserts which may be suitable for the treatment of hemorrhoids, but the shapes are not as well suited for the treatment of an enlarged prostate as the present invention.

SUMMARY OF THE INVENTION

The invention is the shape of the device with the means of adjusting said device to fit snugly between the legs beneath the outside area of the prostate gland. The placement of said device adjacent to the outside area of the prostate gland for a period of time of approximately fifteen minutes causes the prostate gland swelling to reduce thus allowing urine to flow through the urethra, the tube passing through the prostate gland.

In its simplest form the invention comprises a banana-shaped device containing frozen material (such as plain water or the frozen hydrogel identified in U.S. Pat No. 4,563,182, etc.); said device is covered by an insulating material to protect the exposed skin from the frozen material and avoid frost-bite. Said device can vary in size according to the size of the individual. Said device has one bulged end to keep said device from slipping up when pulled close to the body. Said device has a cord attached to the other end to pull said device close to the enlarged prostate.

Prior to use, the entire device is frozen by placing it in a freezer. The individual lies flat on his back, places said device snugly between his legs against the prostate gland and snugs said device by the pull cord.

Said device remains in place for about fifteen minutes after which time it is removed. Immediately thereafter, the subject will be able to urinate more freely.

BRIEF DESCRIPTION OF THE DRAWING

FIG. 1 is a plan view of the present invention PROST-COOL.

DESCRIPTION OF THE PREFERRED EMBODIMENTS

Referring now in detail to the drawing, FIG. 1 shows the present invention PROST-COOL. The invention may be formed of suitable plastic materials or other materials which are approved for medical use by FDA.

Said invention has a cylindrical form about 1 and ¼ inches in diameter and is about 15 inches long. The wall thickness is about 1–5 mils. The above as well as other dimensions given herein are not critical and subject to variations depending upon the material used and method of fabrication.

FIG. 1 also shows the device for adjusting said invention while said invention is in use. The materials used for said second device can vary and may include string, rope, plastic or cloth.

The congealable fluid within said invention may be water or any other type of freezable fluid. The important requirements are a relatively high latent heat of fusion and a freezing temperature below 32 degrees F.

I claim:

1. A portable device for application to a human body comprising:
   a container preformed to facilitate coolant therein to freeze without other forms of support into a curved banana shape sized to snugly fit between the legs beneath the outside area of the prostate with one end bulged to prevent said device from slipping while in said container being sized to externally cool the prostate gland of said body;
   a single cord attached to the other end for adjusting said shape during use of said device sufficient to maintain cooling of said prostate while accommodating changing positions of said body.

2. A device according to claim 1, wherein said single cord includes a draw string, rope, plastic or cloth, to hold device against the prostate.

3. A device according to claim 1 wherein said device is formed of suitable flexible plastic or other materials.

* * * * *